United States Patent
Huh et al.

(10) Patent No.: US 9,394,560 B2
(45) Date of Patent: Jul. 19, 2016

(54) **METHOD OF CULTURING *E. COLI* CELLS FOR HIGH DENSITY**

(71) Applicant: HANMI SCIENCE CO., LTD., Hwaseong-si, Gyeonggi-do (KR)

(72) Inventors: Yong Ho Huh, Seoul (KR); Euh Lim Oh, Seoul (KR); Sung Youb Jung, Suwon-si (KR); Se Chang Kwon, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 0 days.

(21) Appl. No.: 14/384,015

(22) PCT Filed: Mar. 12, 2013

(86) PCT No.: PCT/KR2013/001980
§ 371 (c)(1),
(2) Date: Sep. 9, 2014

(87) PCT Pub. No.: WO2013/137622
PCT Pub. Date: Sep. 19, 2013

(65) Prior Publication Data
US 2015/0050692 A1 Feb. 19, 2015

(30) Foreign Application Priority Data
Mar. 12, 2012 (KR) ........................ 10-2012-0025230

(51) Int. Cl.
*C12P 21/04* (2006.01)
*C12N 1/20* (2006.01)
*C12P 21/00* (2006.01)
*C12P 21/06* (2006.01)
*C12N 15/74* (2006.01)

(52) U.S. Cl.
CPC .. *C12P 21/00* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 6,410,270 B1 | 6/2002 | Strittmatter et al. | |
| 8,093,034 B2 | 1/2012 | Swennen | |
| 2014/0357843 A1* | 12/2014 | Oh et al. | ............ 530/387.3 |

FOREIGN PATENT DOCUMENTS

| | | |
|---|---|---|
| CN | 101258164 A | 9/2008 |
| CN | 101831414 A | 9/2010 |
| EP | 0 511 226 B1 | 3/1995 |
| KR | 10-0235315 B1 | 12/1999 |
| KR | 10-2011-0061521 A | 6/2011 |
| WO | 2007/021129 A1 | 2/2007 |

OTHER PUBLICATIONS

Ramchuran et al., "Production of heterologous thermostable glycoside hydrolases and the presence of host-cell proteases in substrate limited fed-batch cultures of *Escherichia coli* BL21(DE3)" 60 Applied Microbiology and Biotechnology 408-416 (2002).*
Faulkner et al., "Use of Fed-Batch Cultivation for Achieving High Cell Densities for the Pilot-Scale Production of a Recombinant Protein (Phenylalanine Dehydrogenase) in *Escherichia coli*" 27 Biotechnology Progress 889-897 (2006).*
Yari et al., "High level expression of recombinant BoNT/A-Hc by high cell density cultivation of *Escherichia coli*" 35 Bioprocess and Biosystems Engineering 407-414 (Aug. 11, 2011).*
Kim et al., "Two-Step Fed-Batch Culture of Recombinant *Escherichia coli* for Production of Bacillus licheniformis Maltogenic Amylase" 12(2) Journal of Microbiology and Biotechnology 273-278 (2002).*
European Patent Office, Communication dated Sep. 30, 2015, issued in corresponding European Application No. 13760453.4.
The State Intellectual Property Office of the P.R.C., Communication dated Aug. 24, 2015, issued in corresponding Chinese Application No. 201380013931.9.
Zhang et al., "High cell Density Cultivation of Recombinant *Escherichia coli* for Production of Trail by Using a 2-stage Feeding Strategy", Chinese Journal of Biotechnology, May 2004, vol. 20, No. 3, pp. 408-413.
Cen et al., "High Density Culture of Recombinant Bacteria", Bioreaction Engineering, Higher Education Press, Version 1, Sep. 2005, pp. 287-289 (7 pages total).
Jeong et al., "High-level production of a single chain antibody against anthrax toxin in *Escherichia coli* by high cell density cultivation", Bioprocess Biosyst Eng, Feb. 2011, vol. 34, No. 7, pp. 811-817.
Lee et al., "Secretory production of Arthrobacter levan fructotransferase from recombinant *Escherichia coli*", FEMS Microbiology Letters, Jan. 2001, pp. 127-132.
Sang, "High cell-density culture of *Escherichia coli*", Trends in Biotechnology, Elsevier Publications, Mar. 1996, vol. 14, No. 3, pp. 98-105.
Beom Soo Kim et al., "High cell density fed-batch cultivation of *Escherichia coli* using exponential feeding combined with pH-stat", Bioprocess biosyst Eng, 2004, pp. 147-150, vol. 26, No. 3.
Won-Heong Lee et al., "Enhanced production of GDP-L-fucose by overexpression of NADPH regenerator in recombinant *Escherichia coli*", Appl. Microbiol Biotechnol, 2011, pp. 967-976, vol. 91, No. 4.

(Continued)

*Primary Examiner* — Nancy J Leith
(74) *Attorney, Agent, or Firm* — Sughrue Mion, PLLC

(57) ABSTRACT

Disclosed is a method of culturing *E. coli* cells for high density, comprising a cell growth step and an expression induction step by which a maximum of cell mass can be obtained with the concomitant maximum expression of a recombinant protein. *E. coli* transformed to produce a recombinant protein of interest can be grown at a high concentration using the culturing method of the present invention. Therefore, the method increases the productivity of cells as well as the production yield of the recombinant protein, and can be widely applied to the effective production of recombinant proteins.

17 Claims, 2 Drawing Sheets

(56) References Cited

OTHER PUBLICATIONS

Ki Jun Jeong et al. "High-Level Production of Human Leptin by Fed-Batch Cultivation of Recombinant *Escherichia coli* and Its Purification", Applied and Environmental Microbiology, Jul. 1999, pp. 3027-3032, vol. 65, No. 7.

Jaakko Soini et al., "High cell density media for *Escherichia coli* are generally designed for aerobic cultivations—consequences for large-scale bioprocesses and shake flask cultures", Microbial Cell Factories, 11 pages, Aug. 7, 2008, vol. 7, No. 26.

R. Khalilzadeh et al., "Process development for production of recombinant human interferon-γ expressed in *Escherichia coli*", J Ind Microbiol Biotechnol, Feb. 2004, pp. 63-69, vol. 31, No. 2.

Seo, Myung-Ji et al., "Production of a Platelet Aggregation Inhibitor, Salmosin, by High Cell Density Fermentation of Recombinant *Escherichia coli*", J. Microbiol. Biotechnol., 2011, pp. 1053-1056, vol. 21, No. 10.

International Searching Authority, International Search Report of PCT/KR2013/001980 dated Jul. 22, 2013 [PCT/ISA/210].

* cited by examiner

METHOD OF CULTURING E. COLI CELLS FOR HIGH DENSITY

TECHNICAL FIELD

The present invention relates to a method of culturing E. coli cells for high density. More particularly, the present invention relates to a method of culturing E. coli cells for maximizing its proliferation, comprising the step of growing E. coli cells and inducing the expression of recombinant protein in order to maximize the amount of cell mass and recombinant protein.

BACKGROUND ART

E. coli is the most commonly used host cell for for the mass production of various useful proteins due to its high growth rate and advanced techniques in the fields of fermentology and genetic engineering, available for culturing and genetic engineering of E. coli. A high yield production of recombinant protein requires culturing of the transformed E. coli cells in a high density. To this end, various types of media such as a complex medium, synthetic medium, and semi-synthetic medium, and various methods for feeding media such as a constant-rate feeding, a stepwise increase of the feeding rate, an exponential feeding, or specific growth rate control, pH-stat and DO-stat control, and glucose and acetic acid concentration control have been developed and used to obtain high cell densities of E. coli. But, practically, there is a specific method and optimal condition for culturing each of the transformed strain. Thus for a high yield protein production, it is important to select the most optimal method for feeding media and culturing the cells.

In general, in the production of recombinant protein by recombinant E. coli, the characteristics of corresponding promoter and expressed protein affect the cell growth rate and productivity per each unit of the cells. For the system where protein expression is controlled by a strong promoter, a rapid expression of recombinant protein can disrupt the balance of energy metabolism of the host cell, thereby inhibiting the cell growth. Especially, when the expressed protein has a direct negative effect on host cells, it inhibits the growth of the host cells to greater extent.

For these reasons, protein expression under a strong inducible promoter becomes a significant burden to the host cells. Thus as this burden is minimized, the mass production of recombinant protein can be achieved more easily. Considering the above conditions, optimal expression time may vary depending on the characteristics of the expressed protein even when the same type of expression vector and host cells are used for protein expression. In addition, significance of the effects of expression time on cell growth and expression rates may vary. Furthermore, cell growth rate and cell mass affects a protein production. With the same productivity per cell, use of higher mass of cells can increase the yield of protein production. Therefore, it is important to establish optimal culturing conditions for producing the cell mass with a high density in the production of recombinant proteins by recombinant microorganisms.

Since the protein expression of transformed E. coli is closely related to various intracellular physiological/ecological factors related to the growth environment (stability and number of plasmid copies, transcription and translation efficiency, solubility of expressed proteins, proteolysis, membrane integrity, etc.), it is critical to establish an optimal culturing condition to maximize production yield and productivity. Therefore, in order to express a recombinant protein at high yield, an appropriate inducer such as IPTG needs to be added and media with suitable composition for protein production needs to be fed by appropriate method to the culturing media of recombinant E. coli at high density. If needed, the media composition and method of feeding the same have to be modified for recombinant protein production (Yee and Blanch, 1992, Bio/Technol. 10, 1550-1556).

Methods for expressing a recombinant protein in E. coli can be divided into three representative types. The first method is expression of a recombinant protein as a soluble form in the cytoplasm of the E. coli cell. The second method is expression of a recombinant protein to periplasm of the E. coli cell using a signal sequence. The other method is expression of protein in a form of inclusion body(IB), and this method is used most commonly for expressing a protein at a high yield.

When proteins are expressed in an IB form, the E. coli cells need to be cultured in a high density. In detail, with the similar protein expression rate per each cell, as E. coli cells are grown in higher density, the higher yield of protein products can be obtained. Thus there have been many studies on investigating the method to grow E. coli cells into a high density. Korean Patent No. 10-0235315 discloses a use of fusion protein for over-expression of a human growth hormone, but the cell mass was found to be about 90 to 100 g per liter. Furthermore, it is observed that the final absorvance($OD_{600}$) was not higher than 150, in the production process of recombinant protein under the two-step fermentation condition(Microb Cell Fact. 2008 Aug. 7; 7:26). Likewise, a high density-culturing condition for producing protein like salmosin yielded only 65.70 g of IB per liter (J Microbiol Biotechnol. 2011 Oct. 21; (10):1053-6). In addition, culturing condition for producing IFN gamma yielded only about 100 g of cell mass per liter of a cell culture (J Ind Microbiol Biotechnol. 2004 February; 31(2):63-9. Epub 2004 Feb. 19). As a result, there is still a high need for the development of a method of culturing E. coli cells for a higher density.

Based on this background, in an effort to develop a method for producing recombinant protein in a high yield, the present inventors have found that when the host cells are cultured with different types of media between a step of culturing transformed E. coli cells and a step of inducing expression of recombinant protein, a mass production of recombinant protein in the transformed E. coli could be achieved, thereby completing the present invention.

DISCLOSURE OF INVENTION

Technical Problem

It is therefore an object of the present invention to provide a method of culturing E. coli cells for high density.

Solution to Problem

As one embodiment to achieve the object of the present invention, the present invention provides a method of culturing E. coli cells for high concentration.

To be specific, the present invention provides a method of culturing E. coli cells comprises (i) culturing E. coli cells in batch culture mode in cell growth medium until pH of media is increased by 0.1 or higher; (ii) culturing the E. coli cells in fed-batch culture mode with addition of the first feed medium upon the pH increases of the cell culture medium; and (iii) culturing the E. coli cells in fed-batch culture mode with addition of the second feed medium upon the increase of absorbance at 600 nm ($OD_{600}$) of 150 or higher in the cell culture.

For the object of the present invention, the *E. coli* may be the transformed *E. coli* that expresses a recombinant protein.

As used herein the term "cell growth medium" refers to a medium used to grow *E. coli* cells. For the purpose of the present invention, the cell growth medium may comprise an initial culture medium for providing *E. coli* with a growth environment, and a trace metal solution for controlling pH and promoting the growth of *E. coli*, but is not limited thereto. A type of initial culture medium is not limited, but preferably contains tryptone, yeast extract, NaCl, $KH_2PO_4$, and $(NH_4)_2HPO_4$. And the trace metal solution is not limited, but preferably it contains citric acid, $FeCl_2$, $H_3BO_3$, $MnCl_2$, $CuCl_2$, $Na_2MoO_4$, $CoCl_2$, $ZnCl_2$, and EDTA. Further, the cell growth medium may be preferably composed of 20 g/l tryptone, 10 g/l yeast extract, 10 g/l NaCl, 207.5 g/l $KH_2PO_4$, 50 g/l $(NH_4)_2HPO_4$, 268 g/l citric acid, 270 g/l $FeCl_2$, 30 g/l $H_3BO_3$, 100 g/l $MnCl_2$, 15 g/l $CuCl_2$, 25 g/l $Na_2MoO_4$, 25 g/l $CoCl_2$, 20 g/L $ZnCl_2$, and 0.5 M EDTA. Optionally, the cell growth medium may comprise an additional component selected by those skilled in the art.

The method of the present invention may further comprise inducing the expression of the recombinant protein during or after performing the step (iii). Preferably, the *E. coli* may be induced to express a recombinant protein simultaneously with performing the step (iii). More preferably, an inducer for protein expression may be added to the second feed medium. Furthermore, the expression of recombinant protein may be induced by adding isopropyl β-D-1-thiogalactopyranoside (IPTG). More preferably, the concentration of IPTG added may be 0.1 to 0.5 mM. IPTG is preferably added when absorbance of the cell culture at 600 nm ($OD_{600}$) is increased to of 120 or higher.

According to another embodiment, HM11201 (KCCM-10660P), which is an *E. coli* strain transformed to express an immunoglobulin Fc fragment, is cultured in the second feed medium containing IPTG in step (iii) to induce the expression of the recombinant protein. HM11201 is deposited under the Budapest Treaty on the International Recognition of the Deposit of Microorganisms for the Purpose of Patent Procedure on Jun. 20, 2005 at the Korean Culture Center of Microorganisms (KCCM) in Seoul, Republic of Korea and received with an accession number KCCM-10660P.

As used herein, the term "transformed *E. coli*" refers to an *E. coli* strain into which polynucleotide coding for a protein of interest is introduced as it is carried by an expression vector or as it is inserted into the chromosomal DNA, and which can express and produce the recombinant protein of interest. For the purpose of the present invention, no particular limitations are imparted to the polynucleotide, the expression vector, and the recombinant protein to be produced by *E. coli*. As a more convenient expression system, an expression vector containing a Lac operator may be employed. In this case, IPTG (isopropyl β-D-1-thiogalactopyranoside) may be used as an inducer for inducing the expression of a recombinant protein of interest. In one embodiment of the present invention, the transformed *E. coli* is *E. coli* HM11201 (KCCM-10660P), which can express an immunoglobulin Fc fragment (Korean Patent No. 824505).

The term "batch culture" as used in conjunction with bacterial culture, refers to a culturing process in which cells are grown in culture medium comprising the initially supplied materials and nutrient. While suffering from the disadvantage of being unable to supplement nutrients, batch culture enjoys the advantage of guaranteeing a high success rate for a culture of which conditions are impossible to adjust or which is apt to be contaminated. Thus, the batch culture is used mainly in a development phase or at a laboratory level. For the purpose of the present invention, the batch culture is carried out until the transformed *E. coli* cells enter a substantial proliferation phase to increase the cell culture in pH. In this regard, the batch culture is continued to a point of time when the pH of the cell culture is increased by 0.1 from that of the initial culture medium.

The term "the first feed medium", as used herein, refers to a medium which is fed through fed-batch type way at a point of time when *E. coli* starts to proliferate after the batch culture and the pH increases, so as to promote the growth of *E. coli*. For the purpose of the present invention, the first feed medium comprises yeast extract and glucose, and may be added to the cell growth medium. Amounts of yeast extract and glucose in the first feed medium are not particularly limited, but may be properly determined by those skilled in the art. Preferably, the first feed medium contains yeast extract in an amount from 200 to 400 g/l and glucose in an amount from 700 to 800 g/l.

The term "the second feed medium", as used herein, is intended to refer to a medium that is used in fed-batch type culture to induce *E. coli* grown to a certain level to express and produce a recombinant protein of interest. For the purpose of the present invention, the second feed medium comprises yeast extract and glucose and may be added to the cell growth medium. Optionally, the second feed medium may comprise an inducer for inducing the expression of a recombinant protein, such as IPTG. No particular limitations are imparted to amounts of yeast extract, glucose, and IPTG, but they may be determined by those skilled in the art. Preferably, the second feed medium contains yeast extract in an amount from 200 to 400 g/l, and glucose in an amount from 500 to 700 g/l, and optionally IPTG in an amount from 0.1 to 0.5 mM.

The term "fed-batch culture", as used in conjunction with cell culture, refers to a culture process in which a nutrient medium is fed in a controlled manner to a fermentor over the entire fermentation process from the start to the finish of fermentation with no extraction of cell cultures from the fermentor. In a fed-batch type of culture, a nutrient of interest is fed at a rate in proportion to the uptake rate of the microorganism, so that the concentration of the nutrient in the culture can be controlled to a predetermined value. With this advantage, the fed-batch type of culture is employed for research into fermentation with substrate feedback, product feedback or proliferation feedback, and finds applications in the fermentation industry associated with bread yeast, amino acid, antibiotic materials, etc. For the purpose of the present invention, fed-batch culture may be applied to the production of a recombinant protein of interest in *E. coli* grown to a certain level.

Preferably, the culture condition of the present invention may refer to the system where the batch culture and the fed-batch culture are performed as a single process, and not separated.

The method for culturing transformed *E. coli* cells in accordance with the present invention may be a pH-stat process in which the first and a second feed medium are fed sequentially upon a pH increase while recombinant *E. coli* is cultured in a batch culture. In this context, the first feed medium may be fed in a stepwise increment manner while the second feed medium may be fed in a stepwise decrement manner. pH-stat fermentation is a fed-batch process where nutrients are fed when the pH rises as a result of the depletion of nutrients, without considering the concentration of dissolved oxygen. According to DO-stat, nutrients are fed when there is a rise in the concentration of DO which results from depletion of the substrate. For *E. coli*, however, DO-stat fermentation is improper because *E. coli* can grow in both anaerobic and aerobic conditions. In the present invention, only a rise in pH, which indicates the depletion of nutrients, is used as an index of cell growth. Thus, the present invention provides a high cell-density culturing method on the basis of a more accurate reference.

According to the culturing method of *E. coli* in accordance with the present invention, preferably, the first feed medium in step (ii) is fed at a rate from 200 to 400 mL/hr, with stirring at a speed from 400 to 800 rpm, and the second feed medium in step (iii) is fed at a rate from 200 to 400 mL/hr, with stirring at a speed from 400 to 800 rpm. More preferably, the feeding rate of the first feed medium and the stirring speed in step (ii) may be increased stepwise in a range from 200 to 400 mL/hr and a range from 400 to 800 respectively according to the specific growth rates of strain. For example, increasing feeding rate and the stirring speed may involve a total of 3, 4, or 5 steps, and preferably 3 steps. To be more specific the above method may be performed by increasing the feeding rate and the stirring speed of the first feed medium in 3 steps, in which the first feed medium is first fed at a rate from 200 to 300 mL/hr, with stirring at a speed from 400 to 600 rpm, and then at a feeding rate from 250 to 350 ml/hr, with stirring at a speed from 500 to 700 rpm, and lastly at a feeding rate from 300 to 400 ml/hr, with stirring at a speed from 600 to 800 rpm. Specifically, in step 1, the first feed medium is fed at a rate from 200 to 300 mL/hr, with stirring at a speed from 400 to 600 rpm; in step 2, the first feed medium is fed at a rate from 250 to 350 ml/hr with stirring at a speed from 500 to 700 rpm; and in step 3, the first feed medium is fed at a rate from 300 to 400 ml/hr, with stirring at a speed from 600 to 800 rpm. More preferably, the first feed medium may be fed at a rate from 200 to 270 mL/hr, with stirring at a speed from 400 to 550 rpm in step 1; at a rate from 270 to 300 ml/hr, with stirring at a speed from 550 to 650 rpm in step 2; and at a rate from 300 to 350 ml/hr, with stirring at a speed from 650 to 800 rpm in step 3.

Even more preferably, the method of culturing *E. coli* cells in the present invention may be performed as follows: the feeding rate of the second feed medium and the stirring speed in step (iii) which induces the expression of protein through the depletion of nutrient medium, are decreased stepwise with a feeding rate ranging from 200 to 400 mL/hr and a stirring speed ranging from 400 to 800 rpm according to pH changes. For example, decreasing feeding rate and the stirring speed may involve a total of 3, 4, or 5 steps, and preferably 3 steps. To be specific, the above method may be performed by decreasing the feeding rate and the stirring speed of the first medium in 3 steps, in which the first feed medium is first fed at a feeding rate from 300 to 400 mL/hr, with stirring at a speed from 600 to 800 rpm, and then at a feeding rate from 250 to 350 ml/hr, with stirring at a speed from 500 to 700 rpm, and lastly at a feeding rate from 200 to 300 ml/hr, with stirring at a speed from 400 to 600 rpm. Specifically, the second feed medium is fed at a rate from 300 to 400 ml/hr, with stirring at a speed from 600 to 800 rpm in step 1, at a rate from 250 to 350 ml/hr, with stirring at a speed from 500 to 700 rpm in step 2, and at a rate from 200 to 300 ml/hr, with stirring at a speed from 400 to 600 rpm in step 3. More preferably, the second feed medium is fed at a rate from 300 to 350 ml/hr, with stirring at a speed from 650 to 800 rpm in step one, at a rate from 270 to 300 ml/hr, with stirring at a speed from 550 to 650 rpm in step two, and at a rate from 200 to 270 ml/hr, with stirring at a speed from 400 to 550 rpm in step 3.

According to one embodiment of the present invention, the transformed *E. coli* HM11201 is cultured at 37° C. in a trace metal-supplemented growth medium in a batch culture, with aeration at a rate of 1 vvm, and then when the pH rises, the first feed medium is fed to conduct fed-batch culture for 25 to 30 hrs until absorbance at 600 nm ($OD_{600}$) reaches 120 to 180 (Example 1-1). At an $OD_{600}$ of 120 to 180, the second feed medium is fed under various conditions to produce a recombinant protein of interest (Example 1-2). Particularly, inducing the expression of the recombinant protein at an $OD_{600}$ of 150 or higher allows the *E. coli* cells to grow finally to an $OD_{600}$ of 200 or higher and at a density of 200 g/l or higher.

Advantageous Effects of Invention

As described above, *E. coli* transformed to produce a recombinant protein of interest can be grown at a high concentration using the culturing method of the present invention. Therefore, the method of the present invention increases the productivity of cells as well as the production yield of the recombinant protein, and can be widely applied to the effective production of recombinant proteins.

BRIEF DESCRIPTION OF DRAWINGS

(FIG. 1a) The In FIG. 1a, the gray line means temperature, the thick line means pH, the spot line means the speed of stifling, and the thin line means aeration rate.

MODE FOR THE INVENTION

Figure 1A:
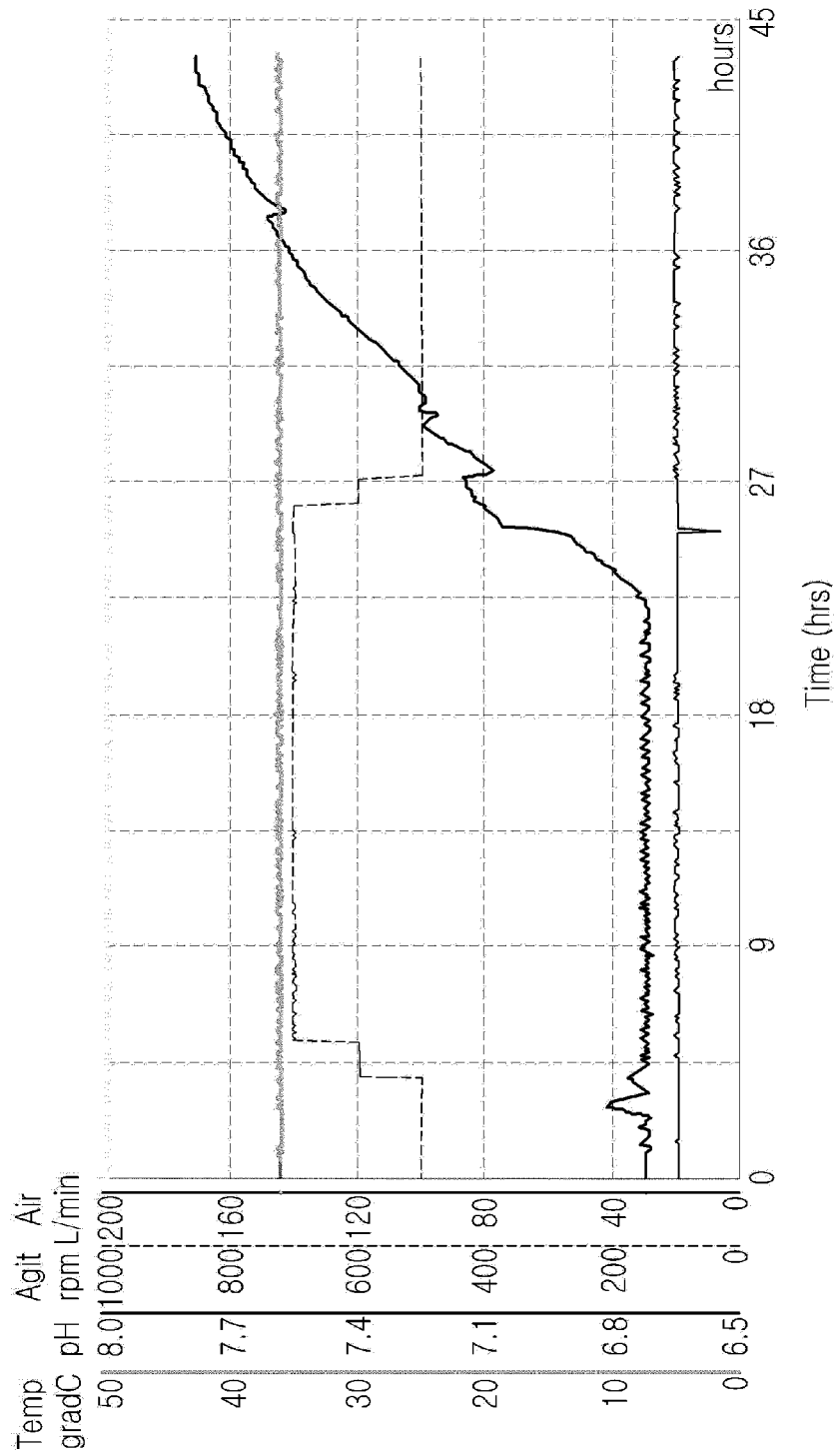
FIG. 1a and FIG. 1b show a growth profile of the transformed *E. coli* HM11201 (KCCM-10660P)(FIG. 1a), and expression levels of a protein as measured by electrophoresis (FIG. 1b), respectively.

A better understanding of the present invention may be obtained through the following examples which are set forth to illustrate, but are not to be construed as limiting, the present invention.

EXAMPLE 1

Fermentation of HM11201

HM11201 (KCCM-10660P), an *E. coli* strain transformed to express an immunoglobulin Fc fragment, was selected as a representative strain and used to optimize medium feeding methods in a stepwise manner according to pH-stat fed-batch fermentation with the aim of achieving high-density cell cultivation and high-yield expression.

EXAMPLE 1-1

Establishment of High-Density Cell Culture Conditions of Transformed *E. coli*

The transformed *E. coli* was cultured at 37° C. in a batch culture in an initial culture medium (tryptone 20 g/l, yeast extract 10 g/l, NaCl 10 g/l, $KH_2PO_4$ 207.5 g/l, $(NH_4)_2HPO_4$ 50 g/l, pH 6.7), with aeration at 1 vvm, and then in a fed-batch manner using the first feed medium (yeast extract 300~400 g/l, and glucose 700~800 g/l) supplemented with a trace metal solution (citric acid 268 g/l, $FeCl_2$ 270 g/l, $H_3BO_3$ 30 g/l, $MnCl_2$ 100 g/l, $CuCl_2$ 15 g/l, $Na_2MoO_4$ 25 g/l, $CoCl_2$ 25 g/l, $ZnCl_2$ 20 g/l, and EDTA 0.5 M).

When the cells are grown to a certain level and the pH of the cell culture has increased to higher than the PID[P(proportional), I(integral), D(differential)] control number, as a result of the depletion of the nutrients in medium, especially carbon source, the changes of metabolism and the growth of *E. coli* and the cell lysis with long-term neglecting occurred. To solve this problem, the feed medium was fed by fed-batch way in a stepwise manner proportionally to the specific growth rate of strain. In the case that the feeding rate of the feed medium exceeds the growth rate of strain, the metabolism and growth of E. coli are inhibited as a result of the accumulation of acetate. Therefore, as the feeding rate is increased in a stepwise manner, the speed of stirring is also increased. In detail, when a 50 l fermentor was employed, in the step where the cell density is higher than $7 \times 10^9$ cells/mL, the first feed medium was fed at a rate of 200 mL/hr to 300 mL/hr with stirring at a speed of 400 to 600 rpm in step 1. On the other hand, in the step where the cell density is $2 \times 10^{10}$ to $3 \times 10^{10}$ cells/mL, the first feed medium was fed at a rate of 250 mL/hr to 350 mL/hr with stirring at a speed of 500 to 700 rpm. Also, in the step where the cell density is $3 \times 10^{10}$ to $4.5 \times 10^{10}$ cells/mL the first feed medium was fed at a rate of 300 to 400 ml/hr with stirring at a speed of 600 to 800 rpm, and when the cell density is higher than $4.5 \times 10^{10}$, the feeding rate of the first feed medium and the speed of stirring was kept constant at the maximum within the range in the growth of cells was not hindered.

Cultivation for 25 to 30 hrs under the said condition allowed the transformed E. coli to grow to an $OD_{600}$ of 120~180.

EXAMPLE 1-2

Establishment of Culture Condition for High-Yield Production of Recombinant Protein To establish optimal conditions for expressing proteins from the E. coli HM11201 cultured in Example 1-1, various compositions were used as the second feed media and fed at various rates.

As a result, a composition comprising yeast extract at a concentration from 200 to 400 g/l and glucose at a concentration from 500 to 700 g/l was found to be useful as the second feed medium for expressing the recombinant protein at a high yield.

Also, the feeding rate of medium and the speed of stirring were reduced in stepwise manner, to convert the process from the growth step of strain to the production step of the recombinant protein, through the depletion of nutrient medium and the control of stirring condition in the fed-batch culture. In detail, the stepwise control of the feeding rate and the stirring speed was controlled proportionally to pH increases and the input of alkaline solution. The feeding rate and the stirring speed were respectively set to be 300 to 400 ml/hr and 600 to 800 rpm for step 1, 250 to 350 ml/hr and 500 to 700 rpm for step 2, and 200 to 300 ml/hr and 400 to 600 rpm for step 3. To induce protein expression, 0.1 to 0.5 mM isopropyl β-D-1-thiogalactopyranoside (IPTG) was added.

Figure 1B:
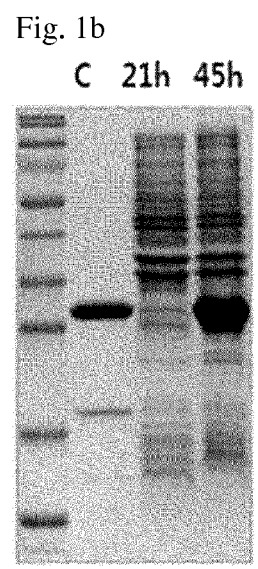

In a late phase of the culture process for promoting the expression of the recombinant protein, E. coli decreases in activity. At this point of time, the addition of an excess of medium caused the dilution of E. coli and the accumulation of acetic acid, reduced the growth of E. coli and thus decreased the expression of the recombinant protein. To resolve these problems, nutrients fed to E. coli were reduced by feeding the feed medium at decreased rates in the late phase of the culture process. Reduced provision with nutrients alters the metabolism of E. coli to cause the release of ammonium ions to the medium which, in turn, increased the pH of the medium. Thus, the cell culture was observed to be maintained at a pH of 6.8 to 7.5 until the culture was completed even when no additional adjustment was made to the consistent pH range (FIG. 1). FIG. 1 shows a growth profile of the transformed E. coli HM11201 (KCCM-10660P), and expression levels of the recombinant protein as measured by electrophoresis. As can be seen in FIG. 1, the production of the recombinant protein of interest from E. coli was increased proportionally to the amount of time given.

Meanwhile, the transformed E. coli was cultured with variations in the composition of feed medium and the feeding time of IPTG. As a result, for E. coli proliferation, when the cells are cultured for a longer period of time during the early phase of culturing to reach a highest possible density of cell culture and then the target recombinant protein expression is induced during the late phase of culturing, the proliferation of E. coli can be maximized, thereby increasing the productivity of the strain (Table 1). After 45 hrs culture, final $OD_{600}$, final cell mass and protein were measured.

TABLE 1

Cell Mass Produced According to Compositions of Medium and Time of Expression Induction.

| Condition | A | B | C | D |
|---|---|---|---|---|
| First Feed Medium | 200 g/L (Yeast), 700 g/L (Glucose) | 200 g/L (Yeast), 700 g/L (Glucose) | 400 g/L (Yeast), 700 g/L (Glucose) | 200 g/L (Yeast), 800 g/L (Glucose) |
| Second Feed Medium | 200 g/L (Yeast), 700 g/L (Glucose) | 400 g/L (Yeast), 500 g/L (Glucose) | 200 g/L (Yeast), 700 g/L (Glucose) | 300 g/L (Yeast), 700 g/L (Glucose) |
| $OD_{600}$ on 20 hrs | 94.7 | 103.0 | 142 | 146 |
| Induction$OD_{600}$ | 20 hr: 94.7 | 25 hr: 122.6 | 25 hr: 163 | 30 hr: 183 |
| Final $OD_{600}$ | 182.4 | 186.6 | 229.2 | 268 |
| Final Cell Mass(g/L) | 184.1 | 189.5 | 207.4 | 263.6 |
| Protein extract(g/L) | 1.72 | — | — | 2.46 |

As is understood from the data of Table 1, a final $OD_{600}$ of 200 or greater, and a cell mass of 200 g or greater, can be obtained according to the composition of the feed medium and the time of expression induction.

As can be seen in FIG. 1, immunoglobulin Fc can be expressed at a high level, with a 1.5-fold increase in cell mass. Therefore, the conditions established in the present invention are effective for enhancing productivity, and the method of the present invention is advantageous in expressing proteins at a high yield.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:
1. A method for culturing E. coli cells transformed with a foreign gene coding for a recombinant protein, comprising:
   (i) culturing the E. coli cells in batch culture mode in a cell growth medium until the pH of the cell growth medium is increased by 0.1 or higher;
   (ii) adding a first feed medium to a cell culture obtained in step (i) and culturing the E. coli cells in pH-stat fed-batch culture mode until an absorbance at 600 nm ($OD_{600}$) of the culture reaches 120 to 180;
   (iii) adding a second feed medium to the cell culture obtained in step (ii) of which the $OD_{600}$ is 150 or higher and culturing the *E. coli* cells in fed-batch culture mode, wherein the pH of the culture during the culturing is increased; and (iv) inducing an expression of the recombinant protein during step (iii), wherein the recombinant protein is expressed only in step (iii) only when the cell culture reaches an $OD_{600}$ value of 150 or higher; and wherein the culturing of step (iii) is conducted to obtain a cell culture having a final $OD_{600}$ value of 200 or higher.

2. The method of claim 1, wherein the transformed *E. coli* strain is HM11201 (KCCM-10660P).

3. The method of claim 1, wherein the transformed *E. coli* strain comprises an expression vector carrying a Lac operator.

4. The method of claim 1, wherein, in step (iv), the expression of the recombinant protein is induced by an addition of isopropyl β-D-1-thiogalactopyranoside (IPTG).

5. The method of claim 4, wherein IPTG is added at a concentration from 0.1 to 0.5 mM.

6. The method of claim 4, wherein, wherein in step (iv), IPTG is added only when the cell culture reaches an $OD_{600}$ value of 150 or higher.

7. The method of claim 1, wherein the first feed medium is fed at a rate from 200 to 400 ml/hr in step (ii), with stirring at a speed from 400 to 800 rpm.

8. The method of claim 7, wherein the feeding rate and the stirring speed are increased stepwise.

9. The method of claim 7, wherein step (ii) is performed by increasing the feeding rate and the stirring speed of the first feed medium in 3 steps, in which the first feed medium is first fed at a rate from 200 to 300 ml/hr, with stirring at a speed from 400 to 600 rpm, and then at a feeding rate from 250 to 350 ml/hr, with stirring at a speed from 500 to 700 rpm, and lastly at a feeding rate from 300 to 400 ml/hr, with stirring at a speed from 600 to 800 rpm.

10. The method of claim 1, wherein the second feed medium is fed at a rate from 200 to 400 ml/hr in step (iii), with stirring at a speed from 400 to 800 rpm.

11. The method of claim 10, wherein the feeding rate and the stirring speed are decreased stepwise.

12. The method of claim 10, wherein step (iii) is performed by decreasing the feeding rate and the stirring speed of the first medium in 3 steps, in which the first feed medium is first fed at a feeding rate from 300 to 400 ml/hr, with stirring at a speed from 600 to 800 rpm, and then at a feeding rate from 250 to 350 ml/hr, with stirring at a speed from 500 to 700 rpm, and lastly at a feeding rate from 200 to 300 ml/hr, with stirring at a speed from 400 to 600 rpm.

13. The method of claim 1, wherein the cell growth medium consists of an initial growth medium comprising tryptone, yeast extract, NaCl, $KH_2PO_4$, and $(NH_4)_2HPO_4$, and a trace metal solution comprising citric acid, $FeCl_2$, $H_3BO_3$, $MnCl_2$, $CuCl_2$, $Na_2MoO_4$, $CoCl_2$, $ZnCl_2$, and EDTA.

14. The method of claim 1, wherein the first feed medium comprises yeast extract at a concentration from 200 to 400 g/l, and glucose at a concentration from 700 to 800 g/l.

15. The method of claim 1, wherein the second feed medium comprises yeast extract at a concentration from 200 to 400 g/l, and glucose at a concentration from 500 to 700 g/l.

16. The method of claim 1, wherein the step (ii) increases a productivity of *E. coli* cells.

17. The method of claim 1, wherein the step (iii) and (iv) increase a production yield of the recombinant protein.

* * * * *